United States Patent [19]
Vaughn et al.

[11] Patent Number: 5,225,786
[45] Date of Patent: Jul. 6, 1993

[54] COMBUSTIBLE GAS SENSOR

[75] Inventors: Eldon D. Vaughn; Samuel C. Creason, both of Fullerton, Calif.

[73] Assignee: Rosemount Analytical, Inc., La Habra, Calif.

[21] Appl. No.: 782,392

[22] Filed: Oct. 25, 1991

[51] Int. Cl.⁵ ........................................... G01R 27/22
[52] U.S. Cl. ..................................... 324/706; 324/693; 422/94
[58] Field of Search ............... 324/706, 693, 724, 725, 324/425, 439, 446, 450; 422/94–97

[56] References Cited

U.S. PATENT DOCUMENTS

| | | | |
|---|---|---|---|
| 2,901,329 | 8/1959 | Kapff | 422/97 X |
| 3,771,960 | 11/1973 | Kim et al. | 422/96 X |
| 4,720,421 | 1/1988 | Khilnani | 422/97 X |

Primary Examiner—Jack B. Harvey
Attorney, Agent, or Firm—John E. Vanderburgh

[57] ABSTRACT

A combustible gas sensor includes a housing defining an interior containing a reference bead and a measurement bead which are fully exposed by the removal of the shroud or can therefrom. The beads are electrically connected in series and the reference bead is connected in parallel with a resister to define one side of a Wheatstone bridge. A liner consisting of a disk defining an inner face and an outer face overlies the reference and measurement beads. The inner face of the disk is provided with a slot opening at the inner face which is dimensioned to receive the reference and measurement beads therein. The slot provides a confined space for fluid communication between the fully exposed beads. A through running opening is disposed in the disk on each side of the slot adjacent the end of the slot in which the reference bead is disposed. A channel extends from each of the openings and communicates with the slot. The upper face of the disk is recessed and in combination with a porous closure defines a plenum in which the sample gas is first received prior to entering the through-running openings in the disk.

4 Claims, 3 Drawing Sheets

COMBUSTIBLE GAS SENSOR

This invention relates to improved sensors for combustible gases and, more particularly, for sensors which detect the presence of the sought for combustible gas by the catalytic combustion of the sought for gas.

BACKGROUND OF THE INVENTION

Instruments for the detection of certain combustible gases such as for example methane, ethylene, hydrogen and the like, normally employ a sensor which includes a pair of detector elements consisting of electrically conductive ceramic coated beads, one of which is a reference bead and the other of which is the measurement bead. The measurement bead is further coated with a catalytic composition, such as for example platinum, which, when contacted by a combustible gas in the presence of oxygen, catalyses an oxidation reaction resulting in the combustion of the gas. The beads are electrically connected in a conventional Wheatstone bridge and combustion of the gas at the measurement bead causes an increase in resistance through the measurement bead which throws the bridge out of equilibrium. The resulting output from the bridge is directly proportional to the concentration of the combustible gas and is read or recorded as an indication of the quantity of the combustible gas present in the sample flowing past the beads.

Conventionally, both the reference bead and the measurement bead are enclosed in shrouds or "cans" which are provided with apertures for communication between the interior of the can and the exterior. The gas sample is introduced through the aperture to the bead within the can. The purpose of the can is to protect the bead and to provide a relatively constant gas and thermal environment. However, the presence of the cans effectively isolates the reference bead from the measurement bead so that the beads may not be exposed to the same or similar compositional or thermal environments. Ambient conditions effect the resistance of the beads and differences in ambient conditions between the reference bead and the measurement bead will produce differences in their resistances due solely to the differing ambient conditions and not due to combustion of a sought for gas. Consequently, the resultant output from the sensor will produce erroneous results.

Although this problem has been recognized in the prior art and attempts have been made to provide a more uniform gas and thermal environment for the reference and the measurement beads. For example, a common practice is to provide a sleeve or cylinder which surrounds the shrouded reference and the measurement beads in an attempt to provide a more uniform gas mixture for contact with the beads within the cans. However, the use of a sleeve, although improving performance, has not proven entirely successful.

SUMMARY OF THE INVENTION

Accordingly, it is an object of the present invention to provide a combustible gas sensor by making more uniform the thermal and compositional environment surrounding the reference bead and the measurement bead.

Another object of the invention is to provide a combustible gas sensor having a broad response over a wide temperature range.

Still another object of the present invention is to provide a combustible gas sensor in which the reference bead and the measurement bead are fully exposed for substantial improvement of fluid communication between the beads.

In accordance with the invention the improved combustible gas sensor includes a housing defining an interior containing a reference bead and a measurement bead which are fully exposed by the removal of the shroud or can therefrom. The beads are electrically connected in series and the reference bead is connected in parallel with a resister to define one side of a Wheatstone bridge. A liner consisting of a disk defining an inner face and an outer face overlies the reference and measurement beads. The inner face of the disk is provided with a slot opening at the inner face which is dimensioned to receive the reference and measurement beads therein. The slot provides a confined space for fluid communication between the fully exposed beads. A through running opening is disposed in the disk on each side of the slot adjacent the end of the slot in which the reference bead is disposed. A channel extends from each of the openings and communicates with the slot. The upper face of the disk is recessed and in combination with a porous closure defines a plenum in which the sample gas is first received prior to entering the through-running openings in the disk.

The sample gas enters the sensors through the porous closure and first contacts the reference bead through the through-running openings and the channels communicating with the slot. After contact with the reference bead the gas passes through the slot to the measurement bead where combustion of the sought for sample occurs. The combustion products then flow back through the slot to the reference bead to provide a uniform thermal environment for both the measurement and the reference bead. The combustion products then exit through the through-running openings and back out through the porous disk. In this fashion, both the reference and the detector beads see a gas of the same composition and also are subjected to the same thermal environment. Unbalancing of the bridge therefore, is due to the increase in resistance at the measurement bead due to combustion and unbalancing of the bridge due to differences in thermal environment between the measurement and reference beads is eliminated.

Other advantages and features of the present invention will become apparent from the detailed description taken in conjunction with the drawings.

DETAILED DESCRIPTION OF THE INVENTION

Figure 1:
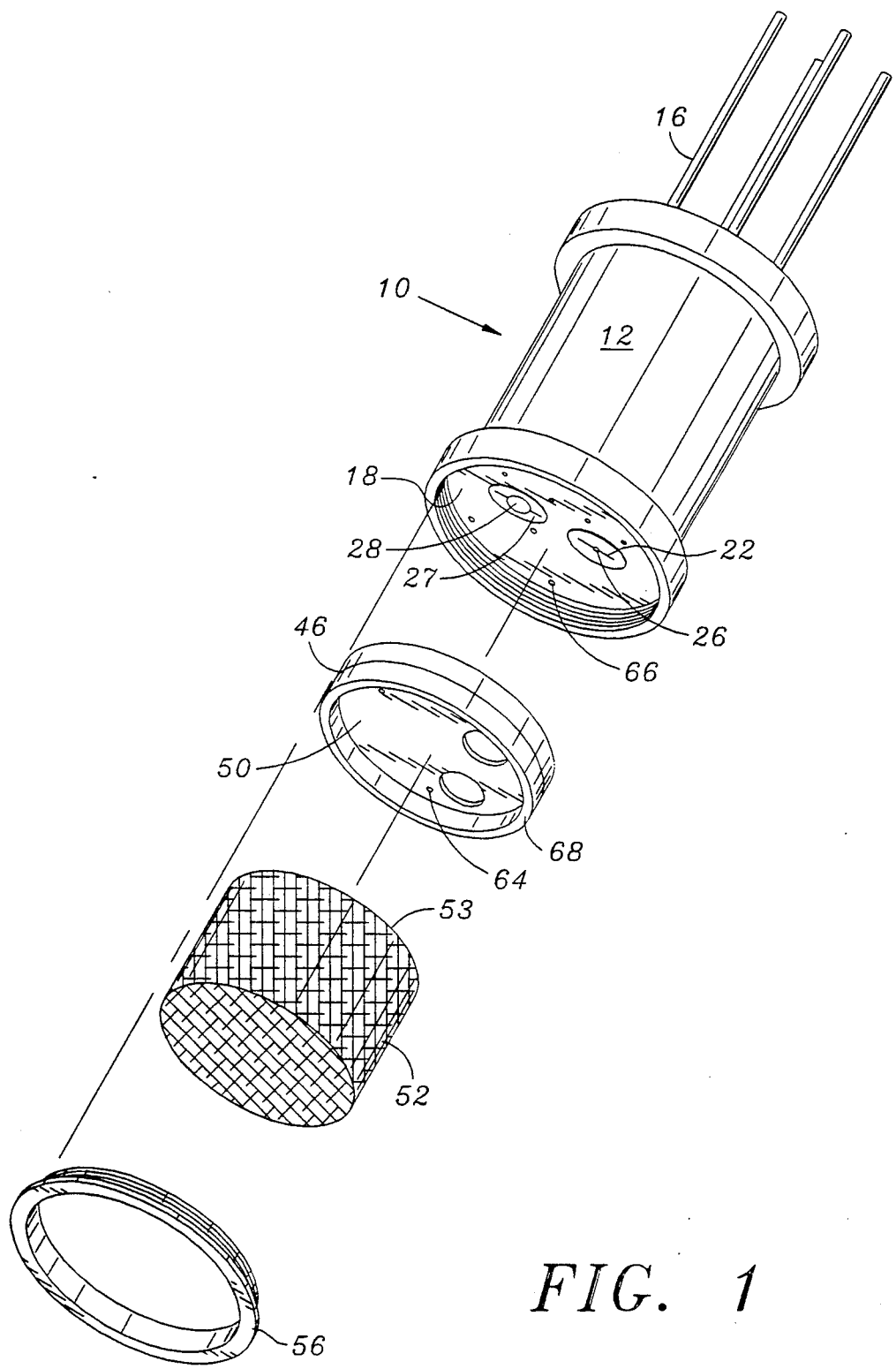
FIG. 1 is an exploded perspective view of a combustible gas sensor constructed in accordance with the present invention.
Figure 2:
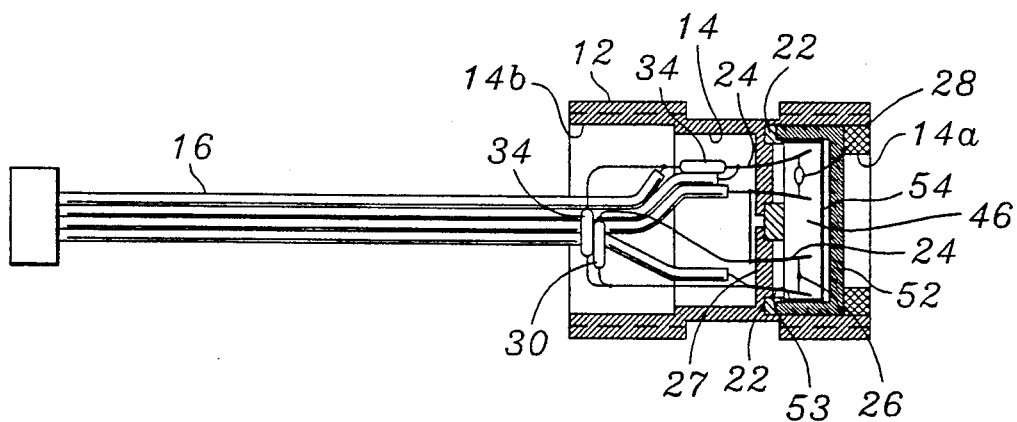
FIG. 2 is a side section of the combustible gas sensor of FIG. 1.
Figure 3:
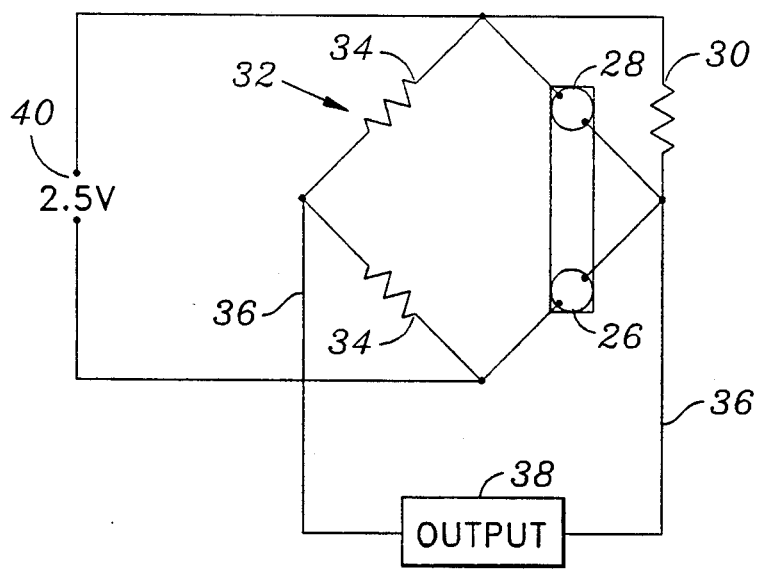
FIG. 3 is a schematic diagram of the bridge circuit for the combustible gas sensor of FIG. 1.
Figure 4:
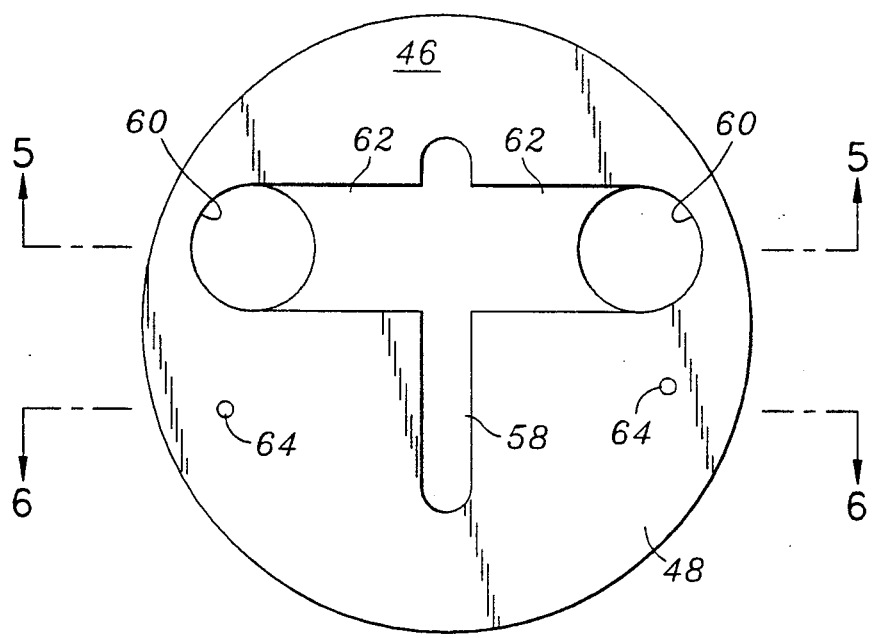
FIG. 4 is bottom plan view of the liner disk of the sensor of FIG. 1.
Figure 5:
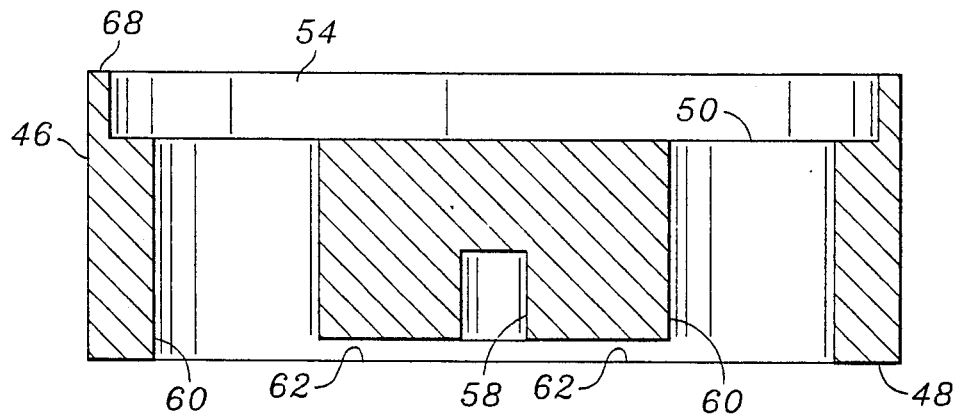
FIG. 5 is a side sectional elevation of the liner disk taken through line 5—5 of FIG. 4.
Figure 6:
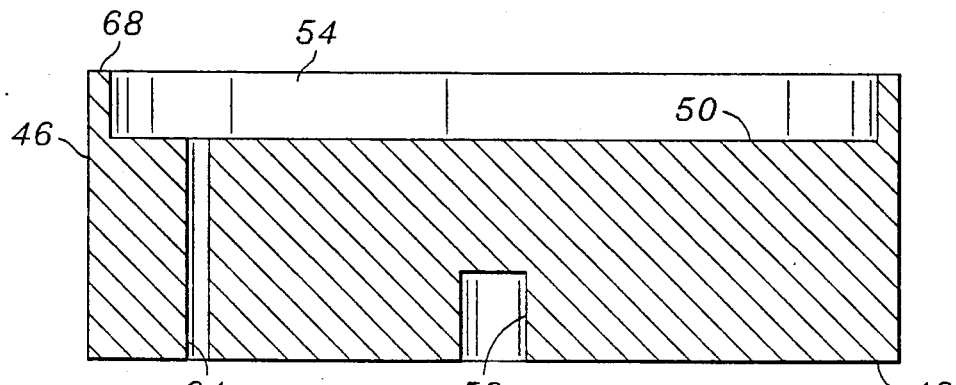
FIG. 6 is a side elevation taken through line 6—6 of FIG. 4.

Referring to FIGS. 1 and 2, there is illustrated a combustible gas sensor, shown generally as 10, constructed in accordance with the present invention which consists of a generally cylindrical housing 12 having a through running bore which defines an interior 14 for receiving electrical conductors 16 and circuitry (FIG. 3) for the sensor 10. A mounting plate 18 is disposed the interior 14 of the housing 12 partitioning the interior 14 into a forward chamber 14a opening at one end of the housing and a rear chamber 14b opening to the opposite end of the housing 12. A pair of apertures 22 are provided in the mounting plate 18 to receive and secure a reference element 26 and a measurement element 28 which are commercially supplied shrouded and mounted in a base 27 through which leads 24 extend. For purposes of description the elements 26 and 28 will hereafter be referred to as beads which is the art recognized descriptor commonly used to describe the elements. The bases carry an annular flange which is larger than the aperture 22 and the base 27 is secured to the mounting plate 18 by bonding the underside of the flange to the mounting plate 18 with a suitable bonding material. Good results are acheived using a commercially available epoxy adhesive. The shrouds or cans are removed from the reference bead 26 and measurement bead 28. The leads 24 are electrically connected to the circuitry (FIG. 3) in the rear chamber 14b. Conductors 16 from a connector housing (not shown) connect the circuitry to a source of power and to an output device 38 (FIG. 3).

As is conventional in the art, the reference bead 26 and the measurement bead 28 are connected in series and the reference bead 26 is connected in parallel with a pad resister 30. The beads are provided by the manufacturer as a matched set and constitute one side of a Wheatstone bridge 32. As illustrated in FIG. 3 the remainder of the Wheatstone bridge 32 comprises a pair of resisters 34 having selected resistances that produce a balanced condition in the bridge 32 when the ambient temperature is about 21° C. and the beads, at their normal operating temperature of about 300° C., are exposed to a non-combustible gas, such as ambient air. The bridge 32 is connected through lines 36 to an output device 38 such as, for example, a high input impedance voltmeter for reading the output voltage of the bridge. The conductors 16 electrically connect the bridge 32 and a source of power 40 such as, for example, a 2.5 volt power source.

The measurement bead 28 is provided with an outer coating of a suitable catalytic material, such as platinum, and the reference bead 26 is passivated to avoid, as much as possible, any reaction with the combustible gas. Both the reference bead 26 and the measurement bead 28 are commercially available and they do not per se form a part of this invention.

In accordance with the invention both the reference bead 26 and the measurement bead 28 are unshrouded and a liner disk 46 defining an inner face 48 and an outer face 50 overlies the beads as will be more fully described hereinafter to provide a confined space for fluid communication between the beads for the purpose to be described. The outer face 50 of the disk is recessed and a porous cup 52 having an open mouth 53 fits into the end of the housing 12 over the disk 46 and when fully assembled, the end of the porous cup 52 is spaced above the outer face 50 of the disk 46 to define a plenum 54 for receiving sample gas. The assembly is completed by a threaded retaining ring 56 which holds the components in place within the housing 12.

Referring now to FIGS. 3-6, the liner disk 46 has an diameter that is slightly less than the inside diameter of the housing 12 so that it fits in the bore of the housing 12 with the inner face 48 contiguous with the mounting plate 18 and there is a space between the edge of the liner disk 46 and the housing wall to permit the open mouth 53 of the porous cup 52 to surround the disk 46. The inner face 48 of the liner disk 46 is provided with a slot 58 which opens on the inner face 48 and which extends essentially across the diameter of the disk 46. The slot 58 is of at least sufficient width and depth to receive the reference bead 26 and the measurement bead 28 when the disk is assembled in the housing 12. Two gas ports 60 extend through and open at the outer face 50 and the inner face 48 of the liner disk 46. The ports 60 are disposed on the liner disk 46 on each side of the slot 58 adjacent the end of the slot 58 in which the reference bead 26 is located. The inner face 48 of the liner disk 46 is also provided with normally running channels 62 between each of the ports 60 and the slot 58 for fluid communication therebetween. In the embodiment shown, a pair of locator holes 64 also extend through the liner disk 46 as an aid to orienting and locating the liner disk 46 during 56 assembly of the sensor 10. The locator holes 64 receive locator pins 66 which are carried on the mounting plate 18.

The peripheral edge 68 of the liner disk 46 at the outer face 50 extends thereabove so that the outer face 50 is recessed. The porous cup 52 overlies the liner disk 46 and cooperates with the extending peripheral edge 68 and the outer face 50 of the liner disk 46 to define a plenum 54 therebetween. The cup 52 comprises a flame resistant material which is sufficiently porous to permit flow through of a gas sample to the interior 14 of the sensor. In addition, the porous cup 52 should be inert with respect to the gas sample being tested and should be flame resistant in view of the combustible nature of the samples being tested. Good results have been achieved using a hundred micron porous surface that produces a bubble stream of water at 1.0 plus or minus 0.5 inches of water pressure. A suitable material has been found to be sintered 316L stainless steel. The assembly is completed by a retaining ring 56 which secures the components in the forward chamber 14a by suitable means, such as for example, by having external threads adapted to engage matching threads in the interior 14 of the housing 12.

The device is assembled by extending the leads 24 of the reference bead 26 and the measurement bead 28 through the apertures 22 in the mounting plate 18 and the beads are secured to the mounting plate 18 as described. The leads 24 are electrically connected in the circuit as described in connection with FIG. 3 by soldering or other similar means. The remainder of the circuit is completed as described and connected to the conductors 16. The liner disk 46 is guided onto the mounting plate 18 by the locator pins 66 in the locator holes 64 and rests on the mounting plate 18 with the reference bead 26 and the measurement bead 28 received in the slot 58. The porous cup 52 is placed over the liner disk 46 and cemented to the mounting plate 18 using a suitable adhesive, preferably epoxy adhesive. The OD of the liner disk 46 is smaller than the OD of the mounting plate 18 to permit the edge 68 of the open end of the porous cup 52 to fit between it and the edge of the mounting plate 18. The mounting plate 18 is then affixed in the housing 12 with the bead, liner and cup assembly in the forward chamber 14a and the circuitry in the rear chamber 14b. The retaining ring 56 is then screwed into place and assembly of the device is completed.

Although not essential, it is preferred that the rear chamber 14b in which the circuitry is located is filled with a suitable potting material to provide mechanical strength and protection for the circuitry. The choice of potting material is not critical any of the commercially available compositions is suitable.

In operation the sample gas is passed through the closed end of the porous cup 52. The gas then passes through the ports 60 to the normally extending channels 62 and into the slot 58 at the location of the reference bead 26. The gas passes through the slot 58 to the measurement bead 28 where any combustible gases contained in the sample are oxidized and generate heat in the measurement bead 28 which raises its resistance. The heated sample gas including combustion products pass back through the slot 58 to contact the reference bead 26 and exits through the channels 62 and the ports 60, through the plenum 54 and back out through the porous cup 52. Combustion at the measurement bead 28 raises its temperature and consequently its resistance thus throwing the bridge 32 out of balance and producing a voltage output. In its simplest form, the voltage output is read directly by a high impedance volt meter although as is well known in the art, the output voltage may be converted to a current signal and subsequently transmitted and digitized for input to a computer or the like.

In accordance with the invention, the flow pattern of the gas sample ensures that both the reference bead 26 and measurement bead 28 are exposed to gases of essentially the same composition since both of the beads are unshrouded and are in direct fluid communication with each other in the slot 58. Likewise, after combustion at the measurement bead 28, the heated combustion products are passed back into contact with the reference bead 26 before exiting the slot 58. In this way temperature within the slot 58 is relatively uniform and both the reference bead 26 and the measurement bead 28 are exposed to similar ambient conditions. Thus, any increase or decrease in ambient temperature at the measurement bead 28 due is likewise sensed by the reference bead 26 and is balanced out.

Since the sensor assembly is often operated at temperatures below freezing, water formed as a combustion product can freeze and in the prior art devices acted to restrict the orifice of the metal can in which the measurement bead 28 was contained. In accordance with the present invention, although water formed during combustion can freeze in the passageways of the porous cup 52, the combined cross sectional area of the pores is significantly large enough that there is substantially no restriction of the flow to the measurement bead 28 and both incoming sample and combustion products flow through the porous cup 52 without restriction sensor output. For this same reason it is preferred that the liner disk 46 be formed of a material which is not readily wetted by water. Good results have been achieved with TEFLON ® liner disks.

As will be understood by those skilled in the art, various arrangements other than those described in detail in the specification, will occur to those persons skilled in the art, which arrangements lie within the spirit and scope of the invention. It is therefor to be understood that the invention is to be limited only by the claims hereto.

Having described the invention, we claim:

1. In a combustible gas sensor having a housing defining an interior containing an electrically conductive reference element and an electrically conducting measurement element coated with a catalyst for the catalytic combustion of a combustible gas and circuitry for measuring the difference in resistance between said measurement element and said reference element as they are heated by combustion of said combustible gas and means for measuring the difference in resistance between said measurement element and said reference element thereby to determine the quantity of combustible gas in a sample, the improvement comprising:

maintaining said reference element and said measurement element in a common confined space for direct fluid communication therebetween wherein said reference element and said measurement element are disposed in one end of a housing member, a disk having an upper and a lower surface and a slot opening in said lower surface is disposed in said one end of said housing with said reference element and said measurement element being received in said slot and said disk having means for introducing gaseous sample to be tested into said slot whereby said gaseous sample freely communicates with both the said reference element and said measurement element.

2. The combustible has detector of claim 1 wherein said means for introducing said gaseous sample comprises an inlet disposed on either side of said slot and axially disposed on said disk adjacent said reference element, a normally extending channel running from said slot to each of said inlets thereby defining fluid communication between said inlet opening and said slot along said inner face of said disk.

3. The combustible gas sensor of claim 1 whereby the peripheral edges of said disk at the upper surface extend thereabove so that said upper surface is recessed and a porous closure is disposed on said extended portions and spaced from the upper surface of said disk thereby to define therebetween a plenum for said sample gas and the combustion products thereof.

4. The combustible gas sensor of claim 3 wherein said porous closure comprises a porous sintered metal cup having an open mouth adapted to surround said liner disk.

* * * * *